United States Patent
Jhon et al.

(10) Patent No.: US 9,442,115 B2
(45) Date of Patent: Sep. 13, 2016

(54) METHOD OF ANALYZING BINDING EFFICIENCY OF ADHESIVE NANOPARTICLES

(71) Applicant: KOREA INSTITUTE OF SCIENCE AND TECHNOLOGY, Seoul (KR)

(72) Inventors: Young Min Jhon, Seoul (KR); Chi Woong Jang, Yongin-si (KR); Myung Suk Chun, Seoul (KR); Seok Lee, Seoul (KR); Jae Hun Kim, Busan (KR); Chul Ki Kim, Samcheok-si (KR); Deok Ha Woo, Seoul (KR); Taik Jin Lee, Seoul (KR); Young Tae Byun, Guri-si (KR); Sun Ho Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 787 days.

(21) Appl. No.: 13/895,708

(22) Filed: May 16, 2013

(65) Prior Publication Data
US 2014/0186851 A1 Jul. 3, 2014

(30) Foreign Application Priority Data

Jan. 3, 2013 (KR) .................. 10-2013-0000695

(51) Int. Cl.
*G01N 33/551* (2006.01)
*G01N 33/574* (2006.01)
*G01N 33/58* (2006.01)

(52) U.S. Cl.
CPC .......... *G01N 33/574* (2013.01); *G01N 33/587* (2013.01)

(58) Field of Classification Search
None
See application file for complete search history.

(56) References Cited

U.S. PATENT DOCUMENTS

2013/0261444 A1* 10/2013 Green .................. A61N 5/062
600/431

FOREIGN PATENT DOCUMENTS

| KR | 10-2011-0041120 | 4/2011 |
| KR | 10-1141410 | 4/2012 |

OTHER PUBLICATIONS

Haun et al, "Quantifying Nanoparticle Adhesion Mediated by Specific Molecular Interactions", Langmuir, 2008, 24, 8821-8832.*

* cited by examiner

*Primary Examiner* — Chris L Chin
(74) *Attorney, Agent, or Firm* — NSIP Law (57) ABSTRACT

Provided is a method of analyzing binding efficiency of adhesive nanoparticles. The method includes (a) injecting a solution containing nanoparticles into a first chamber slide, (b) evaporating only the solution from the first chamber slide into which the solution containing the nanoparticles is injected, and measuring a saturation temperature using a thermal imager while radiating light from a light source, (c) injecting cells into a second chamber slide, (d) injecting a solution containing nanoparticles into the second chamber slide in which the cells are cultured, (e) removing nanoparticles which are not bound to the cells from the second chamber slide into which the cells and the nanoparticles are injected, and (f) evaporating only the solution from the second chamber slide from which the nanoparticles are removed, and measuring a saturation temperature using a thermal image while radiating light from the light source.

5 Claims, 6 Drawing Sheets

METHOD OF ANALYZING BINDING EFFICIENCY OF ADHESIVE NANOPARTICLES

CROSS-REFERENCE TO RELATED APPLICATION

This application claims priority to and the benefit of Korean Patent Application No. 2013-0000695, filed on Jan. 3, 2013, the disclosure of which is incorporated herein by reference in its entirety.

BACKGROUND

1. Field of the Invention

The present invention relates to a method of analyzing binding efficiency of adhesive selective cell-targeting nanoparticles used to treat cancer using a laser and applications thereof.

2. Discussion of Related Art

A method of treating cancer using a photothermal effect through the medium of nanoparticles has attracted much attention as a medical treatment capable of solving not only side effects of surgical operations, radiation therapy, and medicinal therapy, which are conventional cancer treatments, but also aftereffects of the cancer treatments. In addition, a vast amount of research has been conducted on methods of treating cancer using the photothermal effect through the medium of nanoparticles.

A medical laser system has been employed for photothermal treatments using nanoparticles. Although a near infrared laser (NIL) diode system or computed tomography has been applied to conventional laser treatments, since a conventional NIL diode system cannot be controlled according to a temperature of an affected area during treatment and cannot adjust an irradiated area, it is difficult to apply the conventional NIL diode system to surgical operations on living bodies.

To overcome the above-described problems, a treatment apparatus including a new medical laser system and a method of treating diseases using the apparatus have been disclosed in Korean Patent Application No. 10-2011-0041120. The method uses a controller, which may inject nanoparticles into affected areas, such as cancer cells. The nanoparticles may cause plasmonic resonance due to radiation of laser beams. Thereafter, the controller may sense heat generated by a living body due to plasmonic resonance caused by the radiation of laser beams, and obtain thermal image information. Based on the thermal image information, the controller may control the laser system to radiate laser beams at a low intensity to areas suspected as being affected and radiate laser beams at a high intensity to affected areas.

Figure 1:
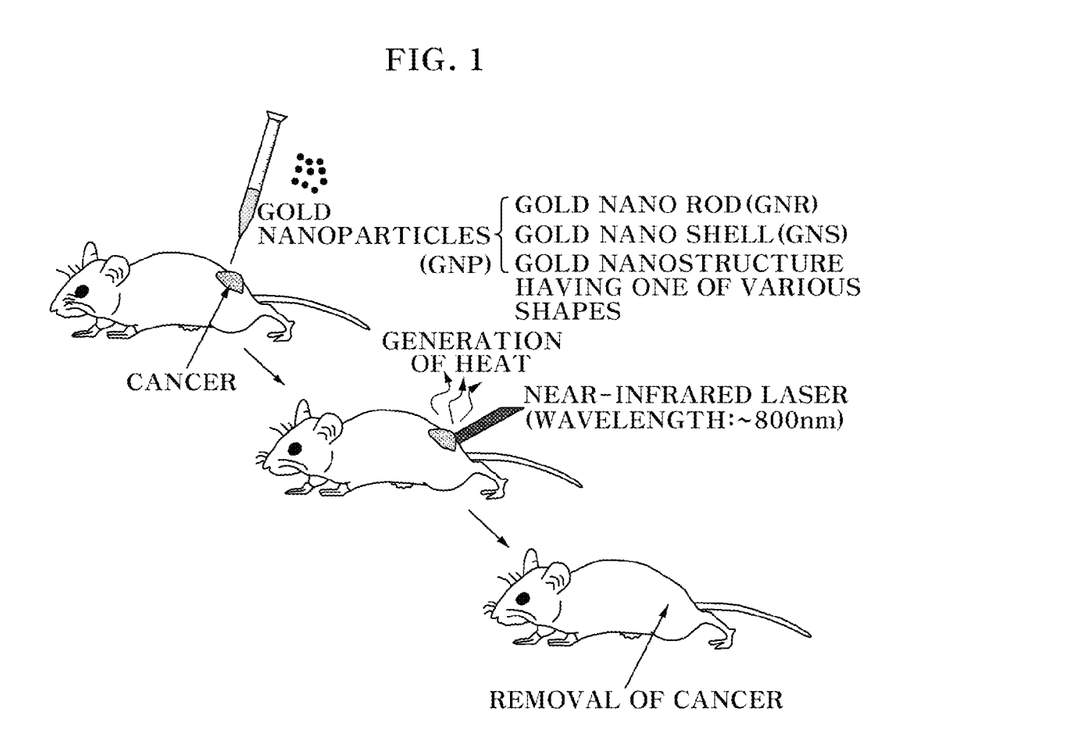
FIG. 1 is a diagram for explaining an example of a cancer treatment method based on a photothermal effect using nanomaterials.

FIG. 1 is a diagram for explaining a cancer treatment using NIL beams. Referring to FIG. 1, it can be seen that a nanomaterial capable of being selectively adsorbed to a specific tissue, such as a cancer tissue, is prepared and injected into a living body using an injector. The nanomaterial may be a noble metal, such as gold (Au) or silver (Ag), and have various forms, such as gold nanorods (GNRs) or gold nanoshells (GNSs). When irradiated with NIL beams, a temperature of only a portion in which gold nanoparticles (GNPs) are selectively adsorbed to the tissue may increase so that cancer can be selectively removed.

The medical laser system using the above-described method may include a laser irradiator configured to radiate laser beams to a living body, a thermal imager configured to sense heat of the living body to which the laser beams are radiated and obtain thermal image information regarding distribution of heat, and a controller configured to control the laser irradiator to radiate laser beams at a low intensity to an area suspected as being affected, sense a portion in which temperature rises due to a reaction of the nanomaterial with the low-intensity laser beams as an affected area based on the thermal image information, and control the laser irradiator to radiate laser beams at a high intensity to the affected area.

The above-described treatment method may involve a nanomaterial capable of inducing plasmonic resonance. Among the results of various research into preparation of nanomaterials, a photosensitizer has been disclosed in Korean Patent Registration No. 10-1141410, which provides a composite of metal nanoparticles and charges and a composition containing the composite used for a photodynamic treatment or diagnosis. The composite may include metal nanoparticles and a charged photosensitizer. The composite is specifically accumulated in tumor tissues, and cannot easily permeate normal tissues. Thus, the composite may effectively destroy only the tumor tissues through a photodynamic treatment.

To utilize a treatment method using plasmonic resonance of a nanomaterial due to laser beams, a considerable amount of research into the shape and size of metal nanoparticles, the wavelength and intensity of NIL beams, and selectivity factors for cancer cells has progressed. However, although it is becoming obvious that nanomaterials administered to treat diseases are harmless to living bodies, there is still no direct proof of the harmlessness of the nanomaterials. Thus, there is still a chance that injecting the nanomaterials into the living bodies presents a risk. Accordingly, when tissues or tumors to which the nanomaterials are to be adhered have small sizes, injecting an excessively large amount of nanomaterials may be inappropriate. The amount of nanomaterials injected to treat diseases should be as small as possible. To minimize the injected amount of nanomaterials, specific nanomaterials, that is, nanomaterials having a strong binding force with respect to cancer cells, should be selected.

Therefore, to apply a treatment method using nanomaterials and a medical laser system, nanomaterials having a strong binding force with respect to cancer cells should be selected in consideration of binding efficiency of the nanomaterials with cancer tissues or cancer cells, that is, the bound amount of nanomaterials per cancer tissue or cancer cell.

SUMMARY OF THE INVENTION

The present invention is directed to a method of analyzing binding efficiency of adhesive selective cell-targeting nanoparticles, which includes measuring binding efficiency of cells with nanoparticles such that the minimum number of nanoparticles is injected to diagnose and treat diseases using a laser.

According to an aspect of the present invention, there is provided a method of analyzing binding efficiency of adhesive nanoparticles, including: (a) injecting a solution containing nanoparticles into a first chamber slide, (b) evaporating only the solvent from the first chamber slide into which the solution containing the nanoparticles is injected, and measuring a saturation temperature using a thermal imager while irradiating light from a light source, (c) injecting cells into a second chamber slide, (d) injecting a solution containing adhesive nanoparticles into the second chamber slide in which the cells are cultured, (e) removing nanoparticles which are not bound to the cells from the second chamber slide into which the cells and the nanoparticles are injected, (f) evaporating only the solvent from the second chamber slide from which the nanoparticles are removed, and measuring a saturation temperature using a thermal image while irradiating light from the light source, and (g) comparing the number of nanoparticles injected into the first chamber slide per area with the number of nanoparticles injected into the second chamber slide per area at a saturation temperature obtained in step (b) as obtained in step (f).

The nanoparticles may be formed of a noble metal capable of generating heat due to a photothermal effect when irradiated with light having a specific wavelength.

In steps (a), (b), and (d) through (f), the saturation temperature may be measured while varying the density of the solution containing the nanoparticles.

The light source may be a lamp or laser having a specific wavelength to induce a photothermal effect of the nanoparticles.

The thermal imager may be an infrared camera or an apparatus configured to perform scanning using a thermal sensor capable of sensing heat at a single point and measure distribution of heat.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

FIG. 2A is an image and a diagram of a system used to measure binding efficiency of nanoparticles according to an exemplary embodiment of the present invention. Referring to FIG. 2A, the system may include a chamber slide, a thermal imager, and a laser irradiator.

Here, the chamber slide refers to a spot into which samples, such as nanoparticles or cells and nanoparticles, are injected. The laser irradiator may be an apparatus configured to radiate laser beams to the chamber slide.

The laser irradiator may include a zoom lens capable of controlling the width of laser beams, so that the intensity of a laser can be controlled. The laser irradiator may be a light source having a specific wavelength to induce a photothermal effect of nanoparticles. In general, it is known that cancer cells are destroyed at a temperature of about 46° C. When cells into which nanomaterials are not injected are irradiated with near-infrared laser (NIL) beams at a low intensity, a temperature of the cells may rise to a temperature of about 30° C. According to an experimental example (refer to FIG. 8), when cells bound to nanomaterials are irradiated with NIL beams, a temperature of the cells may rise up to a temperature of about 58° C.

The thermal imager may be an apparatus configured to sense heat and obtain thermal image information regarding distribution of the heat. The thermal imager may be an industrial thermal imager or an apparatus configured to perform scanning using a thermal sensor capable of sensing heat at a single point and measure a 2-dimensional temperature distribution. The industrial thermal imager may obtain image data regarding distribution of heat expressed by colors according to temperature. In addition, a monitor apparatus configured to receive thermal image information from the thermal imager and display the thermal image information may be included.

FIG. 2B is a schematic view illustrating a method of using a system capable of measuring binding efficiency of nanoparticles. Referring to FIG. 2B, nanoparticles (e.g., gold nanoparticles (GNPs)) may be injected into a cell layer, and a chamber slide filled with a cell medium may be prepared on the cell layer. The prepared chamber slide may be fixed to a sample holder of the system, and irradiated with laser beams. Afterwards, the cell layer may be bound to the GNPs due to the radiated laser beams, and heat may be transmitted to the cell layer due to a photothermal effect of the GNPs. A temperature of the cell layer bound to the GNPs may be measured using a thermal imager.

The nanoparticles may include metal nanoparticles. The metal nanoparticles may include GNPs. The GNPs may broadly include gold nanorods (GNRs), gold nanoshells (GNSs), or gold nanostructures having other shapes.

The nanoparticles may include a noble metal, which may generate heat due to a photothermal effect when irradiated with light having a specific wavelength. The nanoparticles may include a metal as a nanomaterial having each surface with a size of several hundred nm or less. When irradiated with light having a specific wavelength, electrons located in a conduction band of nanoparticles may propagate along boundaries between the nanoparticles, cause collective vibration, and resonate with light (electric field) to generate heat. The nanomaterial may be formed of a gold nanomaterial capable of targeting a specific tissue. After the nanomaterial is directly injected into a target tissue portion or transmitted through blood vessels, the nanomaterial may be used to remove the residual tissue remaining after surgery or to diagnose or treat a metastatic area.

When the nanomaterial applied to an affected area is irradiated with laser beams, the nanomaterial may induce plasmonic resonance to generate heat. Even if the same amount of nanomaterial is injected into the affected area, as the nanomaterial is bound to the cell layer more effectively, more heat may be generated.

Accordingly, by verifying binding efficiency of the nanomaterial with the cell layer, a nanomaterial having a high binding efficiency may be selected. When the selected nanomaterial is used, even if a smaller amount of nanomaterial is injected into a living body, such as cancer, it may become easier to reach a temperature at which cancer cells may be destroyed. Thus, treatment effects may be obtained even with only a small amount of nanomaterial. Accordingly, it is important to functionalize and prepare a nanomaterial that is highly adhesive only to specific cells. Also, when a specific nanomaterial having a strong binding force with respect to each specific cancer cell is prepared, the specific nanomaterial may be injected in a small amount into the specific cancer cell serving as a target. As a result, according to the present invention, only a minimum amount of nanomaterial may be injected so that a laser treatment method using a photothermal effect, which is not destructive to normal cells but destructive only to cancer cells, can be used more stably.

Figure 3:
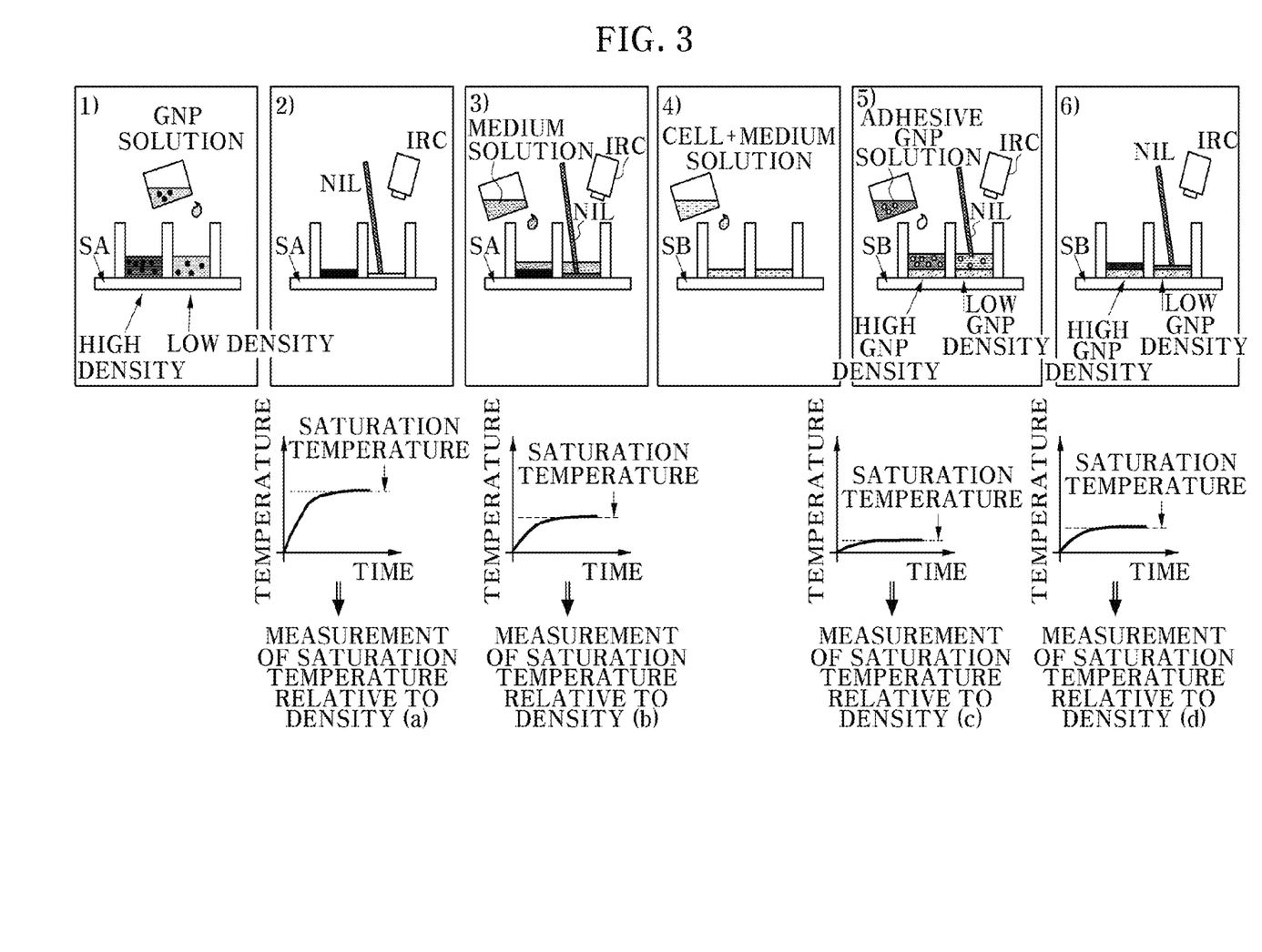
FIG. 3 is a diagram for explaining an example of a method of measuring binding efficiency of nanoparticles according to an exemplary embodiment of the present invention.

FIG. 3 is a diagram for explaining an example of a method of measuring binding efficiency of nanoparticles according to an exemplary embodiment of the present invention.

Here, the density of nanoparticles is indicated by the number of particles per ml, and the density of nanoparticles is indicated by the number of nanoparticles per area (particles/mm$^2$). A saturation temperature refers to a temperature at which a heat generation temperature does not rise any more when laser beams are radiated to a chamber slide into which nanoparticles or both nanoparticles and cells are injected. In general, the saturation temperature rises with an increase in the density of nanoparticles. Cells bound to the nanoparticles may typically be tumor cells. In an exemplary embodiment of the present invention, the cells bound to the nanoparticles may be thyroid cancer cells.

Figure 4:
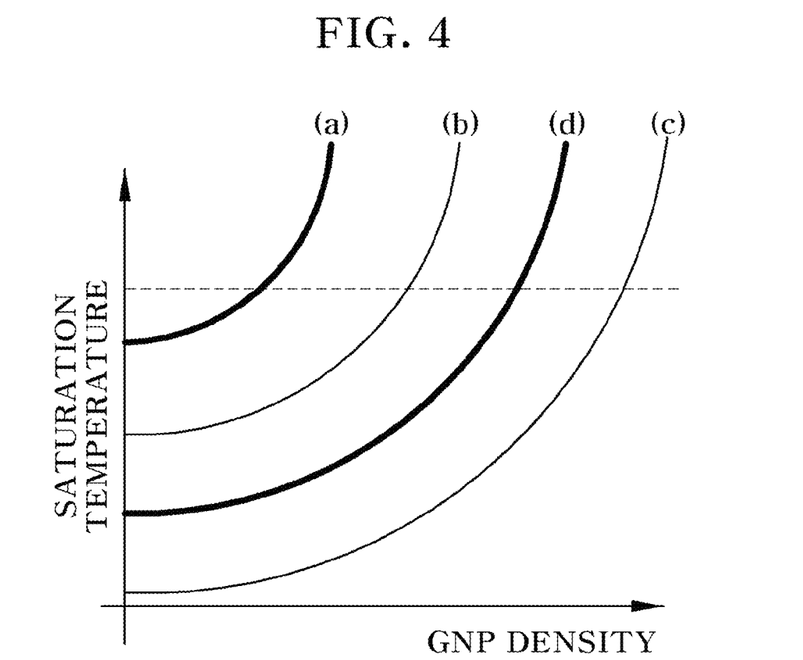
FIG. 4 is a graph showing absorption efficiency of nanoparticles measured by calculating the number of nanoparticles.

Referring to FIG. 3, to begin with, a solution containing nanoparticles, for example, a GNP solution, may be injected into a first chamber slide SA (refer to 1) of FIG. 3). Thereafter, only the solvent may be evaporated from the first chamber slide SA. As a result, nanoparticles may be uniformly distributed on a bottom surface of the first chamber slide SA. Next, while irradiating laser (near-infrared laser (NIL)) beams from a laser apparatus to the first chamber slide SA, a variation in temperature at which nanoparticles generate heat may be measured over time using a thermal imager (refer to 2) of FIG. 3). During the radiation of laser beams, the temperature at which the nanoparticles generate heat may constantly rise over time and then may not rise any longer when the temperature reaches a specific temperature. The specific temperature is referred to as a saturation temperature. FIG. 4 is a graph showing absorption efficiency of nanoparticles measured by calculating the number of nanoparticles. Referring to FIG. 4, when the saturation temperature was measured while varying the density of nanoparticles injected into the first chamber slide SA, a curve (a) of FIG. 4 was obtained, and the saturation temperature showed a tendency to increase with a rise in the amount of nanoparticles.

Next, cells may be injected into a second chamber slide SB (refer to 4) of FIG. 3). Thereafter, a solution containing nanoparticles (e.g., GND solution) may be injected into the second chamber slide SB (refer to 5) of FIG. 3). Thereafter, nanoparticles which are not bound to the cells may be removed from the second chamber slide SB, and the solvent may be evaporated from the second chamber slide. As a result, nanoparticles bound to the cells may be distributed on the second chamber slide SB. Next, while radiating laser (NIL) beams from a laser apparatus to the second chamber slide, a variation in temperature at which the nanoparticles generate heat may be measured over time using a thermal imager (refer to 6) of FIG. 3). Similarly, during the radiation of laser beams, the temperature at which the nanoparticles generate heat may constantly rise over time and then may not rise any longer when the temperature reaches a saturation temperature. When the saturation temperature was measured while varying the density of nanoparticles injected into the second chamber slide SB, a curve (d) of FIG. 4 was obtained, and the saturation temperature showed a tendency to increase with a rise in the amount of nanoparticles.

Next, the same saturation temperature may be selected from the variations in temperature obtained from the first and second chamber slides through the above-described steps. Thereafter, at the same saturation temperature, the number of nanoparticles injected into the first chamber slide SA may be compared with the number of nanoparticles injected into the second chamber slide SB. In this case, as a difference between the numbers of nanoparticles to be compared is smaller, a binding force of the nanoparticles to cells may be higher. Referring to FIG. 4, cell binding efficiency is indicated by a difference between GNP density shown in curve (a) and GNP density shown in curve (d) at the same saturation temperature. As the difference between the GNP densities (a) and (d) is bigger, cell binding efficiency may be lower. Conversely, as the difference between the GNP densities (a) and (d) is smaller, cell binding efficiency may be higher.

Since the saturation temperature of the first chamber slide SA is a temperature at which all the nanoparticles injected into the first chamber slide SA generate heat, the saturation temperature of the first chamber slide SA may refer to a temperature at which 100% of the nanoparticles are bound to cells. Since the saturation temperature of the second chamber slide SB is a temperature at which nanoparticles bound to cells, out of the nanoparticles injected into the second chamber slide SB, generate heat, the number of the nanoparticles injected to reach the saturation temperature of the second chamber slide SB refers to the number of nanoparticles to be injected to reach the saturation temperature.

Accordingly, as a difference between the numbers of the nanoparticles injected into the first and second chamber slides SA and SB to reach the same saturation temperature is smaller, a binding force of the nanoparticles with the cells may be higher. When specific nanoparticles have a weak binding force with respect to cells, a larger number of nanoparticles should be injected to reach a saturation temperature required for treatments.

As shown in the examples of FIGS. 3 and 4, the method of the present invention may include a method of measuring binding efficiency of nanoparticles by measuring a saturation temperature while varying a density (particles/ml) of a solution containing the nanoparticles. Thus, binding efficiency of the nanoparticles may be measured at a specific temperature required for treatments. In addition, when a saturation temperature is measured while varying a density of the nanoparticles in the solution containing the nanoparticles, a saturation temperature relative to the density of the nanoparticles may be found. As a result, binding efficiency relative to saturation temperature may be measured.

Experimental Example

Measurement of Binding Efficiency of Adhesive GNPs

Figure 2:
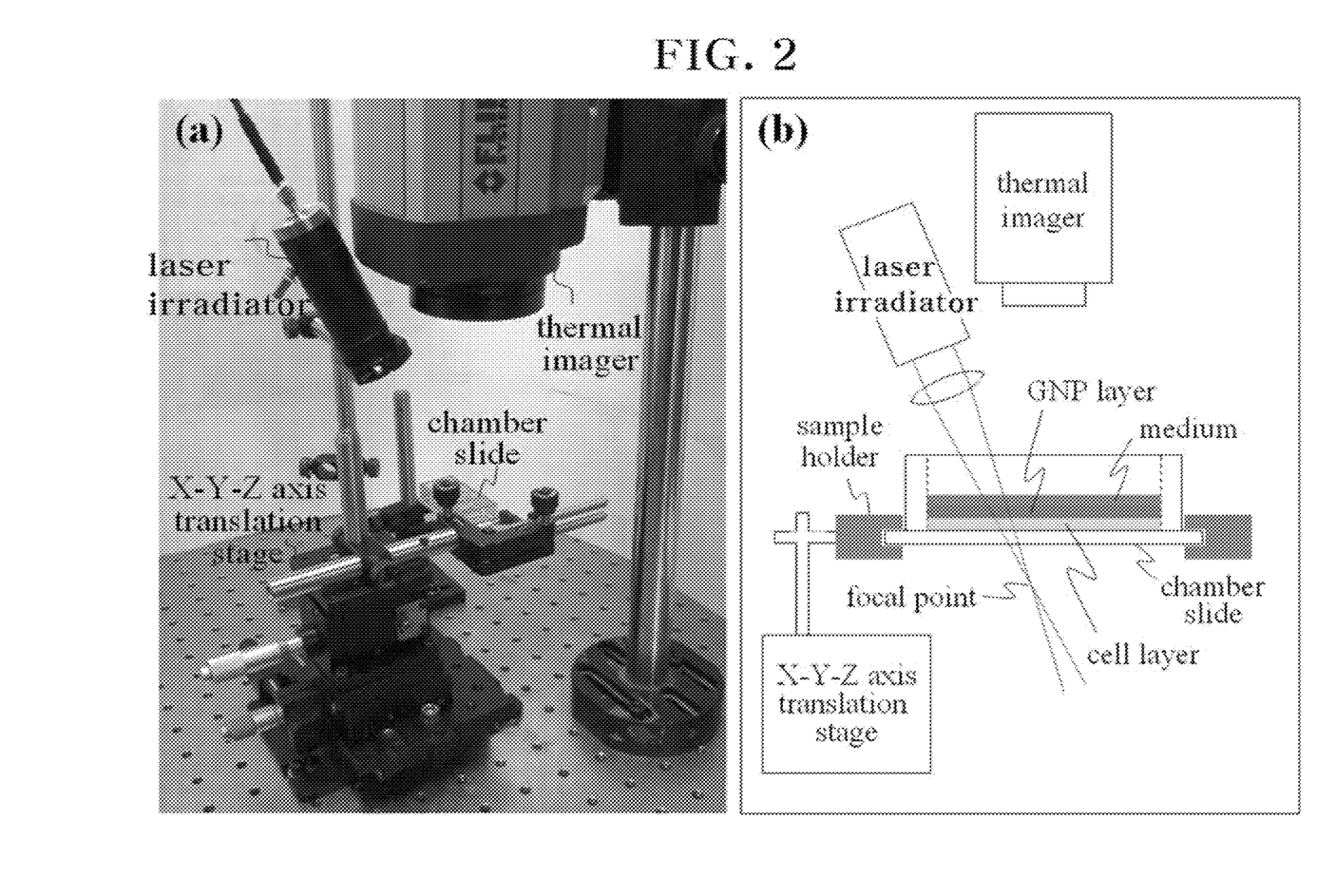
FIG. 2A is an image and a diagram of a system used to measure binding efficiency of nanoparticles according to an exemplary embodiment of the present invention.
FIG. 2B is a schematic view illustrating a method of using a system capable of measuring binding efficiency of nanoparticles.

Binding efficiency of adhesive GNPs was measured using the binding efficiency measuring system of FIG. 2. Target cells whose binding efficiency was to be measured were thyroid cancer cells, laser beams having a wavelength of about 768 nm were radiated, and a saturation temperature was measured by radiating the laser beams while varying a density of GNPs.

Figure 5:
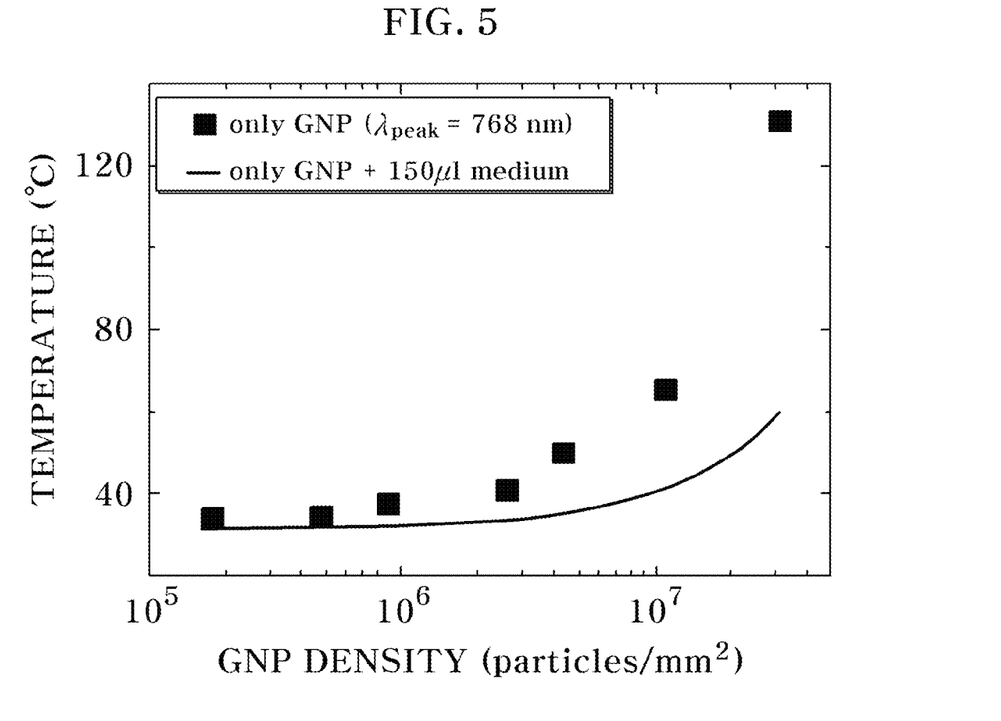
FIG. 5 is a graph showing a variation in saturation temperature measured while varying the density of gold nanoparticles (GNPs), using a binding efficiency measuring system of FIG. 2.

FIG. 5 is a graph showing a variation in saturation temperature measured while varying the density of GNPs using the binding efficiency measuring system of FIG. 2. A solution containing GNPs (or GNP solution) was injected into a first chamber slide, and only the solution was evaporated from the first chamber slide. Thereafter, a variation in temperature was measured using a thermal imager while radiating laser beams to the first chamber slide.

Referring to FIG. 5, black square spots indicate measurements of saturation temperature obtained while varying the density of GNPs. It could be confirmed that a saturation temperature sharply jumped around a density of about $10^7$ particles/mm$^2$.

Figure 6:
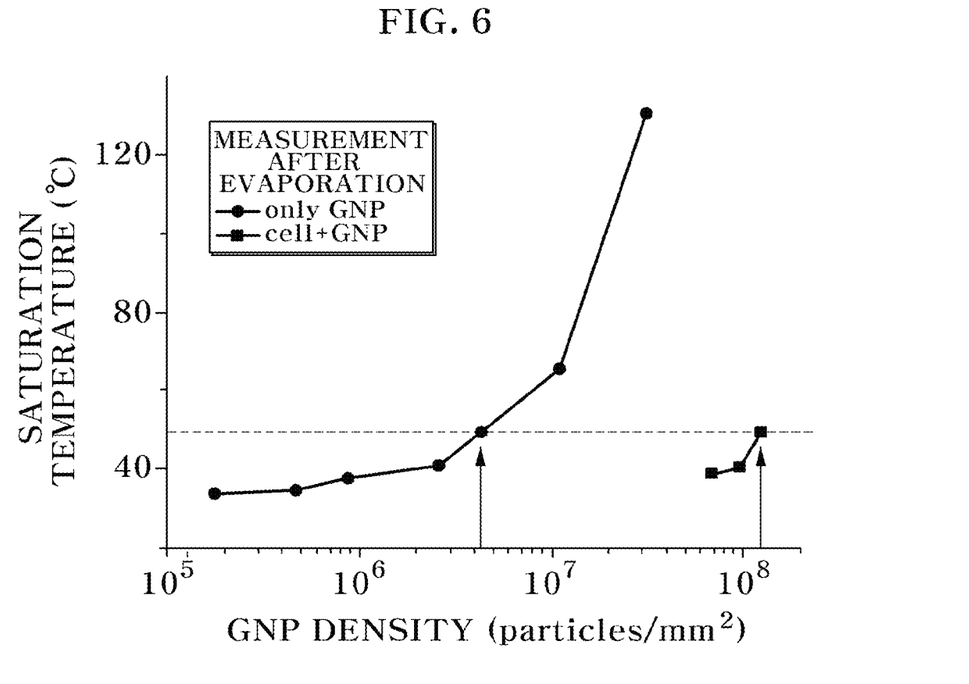
FIG. 6 is a graph showing a variation in saturation temperature measured by injecting only GNPs into cancer cells contained in a first chamber slide while varying the number of the GNPs and a variation in saturation temperature measured by injecting cells into a second chamber slide and injecting adhesive GNPs while varying the number of the adhesive GNPs, using the binding efficiency measuring system of FIG. 2.

FIG. 6 is a graph showing a variation in saturation temperature measured by injecting only GNPs into cancer cells contained in the first chamber slide while varying the density of the GNPs and a variation in saturation temperature measured by injecting cells into the second chamber slide and injecting GNPs while varying the density of the GNPs. The graph of FIG. 6 was obtained using the binding efficiency measuring system of FIG. 2. After injecting a solution containing the GNPs (or GNP solution) into the first chamber slide, only the solution was evaporated. Thereafter, a variation in temperature was measured using a thermal imager while radiating laser beams into the first chamber slide. Also, after the cells were injected into the second chamber slide and a solution containing the GNPs (or GNP solution) was injected, nanoparticles that were not bound to the cells were removed, and the solution was evaporated. Afterwards, a saturation temperature was measured using the thermal imager while radiating laser beams to the second chamber slide. Referring to FIG. 6, at a saturation temperature of about 50° C., the density of the GNPs injected into the first chamber slide was about $4 \times 10^6$ particles/mm$^2$, while the density of the GNPs injected into the second chamber slide was about $1.5 \times 10^8$ particles/mm$^2$. A difference between the densities of the GNPs injected into the first and second chamber slides refers to efficiency of binding of the GNPs with the cancer cells.

Examples of Photothermal Treatments Using Nanoparticles

When selected nanoparticles were applied to cancer treatments using a laser photothermal treating system according to the present invention, treatment effects were confirmed. After the nanoparticles were injected into cancer cells containing a medium and irradiated with NIL beams, a temperature at which the nanoparticles generated heat was measured using a thermal imager, and a fluorescence image captured after the radiation of the NIL beams was confirmed.

Figure 7:
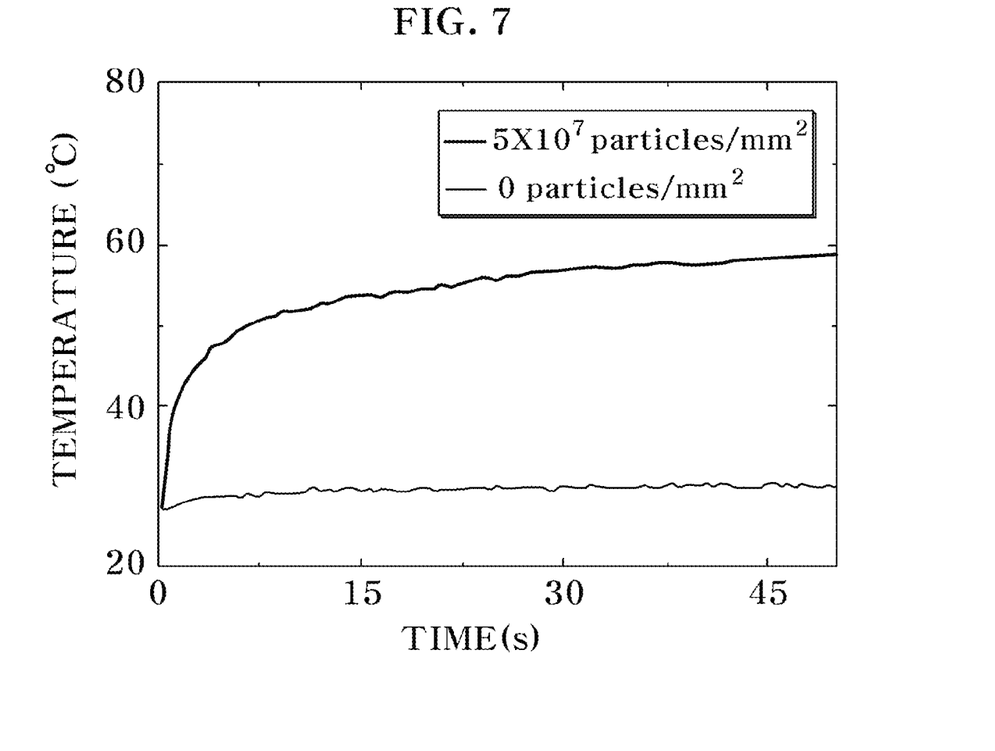
FIG. 7 is a graph showing a variation in temperature of cancer cells measured by radiating laser beams to cancer cells into which GNPs were injected and cancer cells into which GNPs were not injected.

FIG. 7 is a graph showing a variation in temperature of cancer cells measured by radiating laser beams to cancer cells into which GNPs were injected and cancer cells into which GNPs were not injected. Referring to FIG. 7, when the GNPs were injected, it could be confirmed that the temperature of the cancer cells rose up to a temperature of about 58° C. When the GNPs were not injected, it could be confirmed that the temperature of the cancer cells remained at a temperature of about 30° C. and no photothermal effect was produced.

Figure 8:
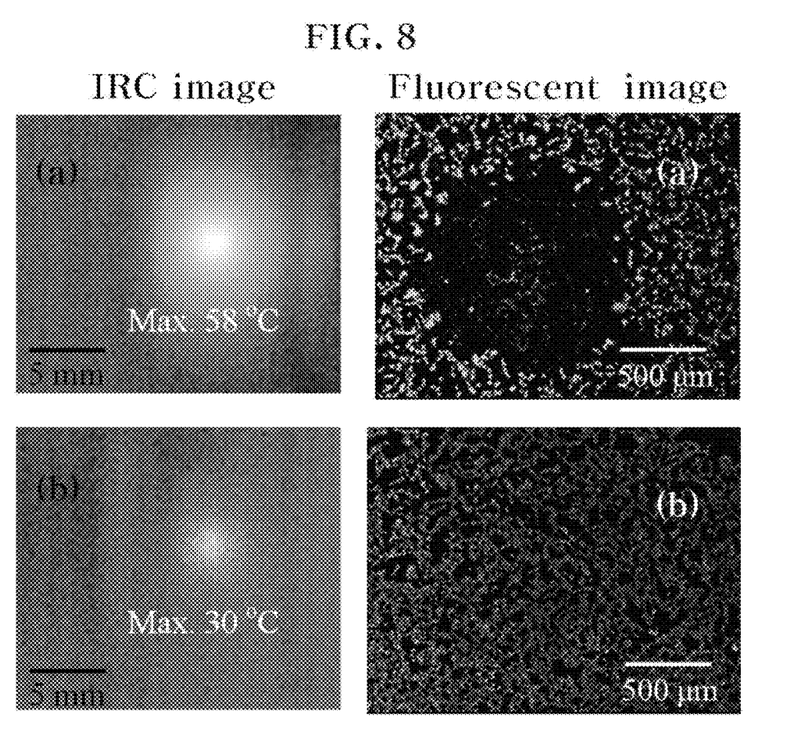
FIG. 8 shows thermal images and fluorescence images showing temperatures of cancer cells measured by radiating laser beams to the cancer cells into which GNPs were injected and the cancer cells into which GNPs were not injected, as shown in FIG. 7.

FIG. 8 shows thermal images and fluorescence images showing temperatures of cancer cells measured by radiating laser beams to cancer cells (a) into which GNPs were injected and cancer cells (b) into which GNPs were not injected, as shown in FIG. 7. Referring to the images of FIG. 8, when the GNPs were injected into the cancer cells (a), a photothermal effect could be confirmed via a thermal image, and destruction of thyroid cancer cells could be confirmed via a fluorescent image. In contrast, when the GNPs were not injected, it could be confirmed that little change occurred in the cancer cells.

According to the present invention as described above, adhesive nanoparticles having a high binding efficiency with respect to specific cancer cells or tissues can be selected, and an injected amount of nanoparticles can be minimized. Furthermore, when a photothermal treatment using a laser is performed by applying the selected adhesive nanoparticles to an affected area, cancer treatments can be performed without causing side effects and aftereffects of surgical operations, radiation therapy, and medicinal therapy.

It will be apparent to those skilled in the art that various modifications can be made to the above-described exemplary embodiments of the present invention without departing from the spirit or scope of the invention. Thus, it is intended that the present invention cover all such modifications provided they come within the scope of the appended claims and their equivalents.

What is claimed is:
1. A method of analyzing binding efficiency of adhesive nanoparticles, comprising the steps of:
 (a) injecting a solution containing nanoparticles into a first chamber slide;
 (b) evaporating only the solvent from the first chamber slide into which the solution containing the nanoparticles is injected, and measuring a saturation temperature using a thermal imager while irradiating light from a light source;
 (c) injecting cells into a second chamber slide;
 (d) injecting a solution containing adhesive nanoparticles into the second chamber slide in which the cells are cultured;
 (e) removing the nanoparticles which are not bound to the cells from the second chamber slide into which the cells and the adhesive nanoparticles are injected;
 (f) evaporating only the solvent from the second chamber slide from which the nanoparticles are removed, and measuring a saturation temperature using a thermal image while irradiating light from the light source; and
 (g) comparing the number of nanoparticles injected into the first chamber slide per area with the number of nanoparticles injected into the second chamber slide per area at the same saturation temperature obtained in step (b) as obtained in step (f).

2. The method of claim 1, wherein the nanoparticles are formed of a noble metal capable of generating heat due to a photothermal effect when irradiated with light having a specific wavelength.

3. The method of claim 1, wherein, in steps (a), (b), and (d) through (f), the saturation temperature is measured while varying the density of the nanoparticles.

4. The method of claim 1, wherein the light source is a lamp or laser having a specific wavelength to induce a photothermal effect of the nanoparticles.

5. The method of claim 1, wherein the thermal imager is an infrared camera or an apparatus configured to perform scanning using a thermal sensor capable of sensing heat at a single point and measure distribution of heat.

* * * * *